United States Patent [19]

Tsao et al.

[11] Patent Number: 4,480,475
[45] Date of Patent: Nov. 6, 1984

[54] REAL-TIME ULTRASONIC WELD INSPECTION METHOD

[75] Inventors: Mike C. Tsao, Groton, Conn.; James F. Mancuso, Murrysville, Pa.

[73] Assignee: Westinghouse Electric Corp., Pittsburgh, Pa.

[21] Appl. No.: 461,883

[22] Filed: Jan. 28, 1983

[51] Int. Cl.³ ............................................. G01N 29/04
[52] U.S. Cl. ......................................... 73/610; 73/614; 219/130.21
[58] Field of Search ................. 73/609, 610, 612, 615, 73/618, 620, 627, 629, 614; 219/109, 130.01, 130.21

[56] References Cited

U.S. PATENT DOCUMENTS

| | | | |
|---|---|---|---|
| 3,384,733 | 5/1968 | Burbank et al. | 219/109 |
| 3,587,300 | 6/1971 | Fuji | 73/629 |
| 3,673,860 | 7/1972 | Flaherty et al. | 73/609 |
| 3,726,130 | 4/1973 | Hurlebaus | 73/629 |
| 4,099,045 | 7/1978 | Okuda et al. | 219/109 |

FOREIGN PATENT DOCUMENTS 19982   2/1981   Japan .............................. 219/130.21

*Primary Examiner*—James J. Gill
*Attorney, Agent, or Firm*—L. A. DePaul

[57] ABSTRACT

The ultrasonic weld inspection method comprises transmitting an ultrasonic wave through the molten metal portion of the weld while the weld is being formed and determining if a weld defect is present in the molten metal. If no defect is detected in the molten metal, the welding process continues. However, if a defect is detected in the molten metal, the welding electrodes remain at that position until the defect has dissipated. In this manner, defects are removed from the weld before the weld metal solidifies.

2 Claims, 5 Drawing Figures

FIG. I

REAL-TIME ULTRASONIC WELD INSPECTION METHOD

BACKGROUND OF THE INVENTION

This invention relates to ultrasonic welding inspection methods and particularly to in-process nondestructive ultrasonic welding inspection methods.

There are many methods known in the art for ultrasonically inspecting welded members. Some of these methods are used during the welding process to inspect the welded joint. For example, an ultrasonic transmitter may be positioned on one electrode and an ultrasonic receiver positioned on another electrode, with the members to be welded positioned between the electrodes. In this method, the ultrasonic wave is transmitted from the ultrasonic transmitter through the weld to the ultrasonic receiver for inspecting the welded joint.

In another type of ultrasonic weld inspection, one ultrasonic transducer can function as both the transmitter and receiver for reflecting ultrasonic waves through the weld joint for inspection.

In U.S. Pat. No. 4,099,045 to Okuda et al. there is described an ultrasonic method for resistance welding. In the Okuda et al. method, an ultrasonic vibrator disposed on one of two opposed electrodes having two metallic plates sandwiched between them for being welded intermittently delivers a pulse-shaped ultrasonic wave to a reflecting surface located in the other electrode and receives the wave reflected from the reflecting surface. The vibrator converts the received wave to an electrical signal that is applied to a minimum sensor and a peak sensor, the minimum sensor senses and holds the minimum peak magnitude of the signal which is then subtracted from the peak magnitude of a similar signal developed within the peak sensor at the time of termination of the welding current. The resulting difference between the two magnitudes determines the weld condition of the welded plates.

Although many of the methods known in the art for ultrasonically inspecting a weld have provisions for inspecting during the welding process, those methods generally involve detecting a weld defect during the welding process and taking corrective action to eliminate the defect after the weld metal has solidified. Typically, the corrective action may be to reject the welded members or to reweld the defective area. Of course, this type of corrective action is expensive in both time and materials and may, nevertheless, result in a less than satisfactory weld due to problems related to reheating of the base metal.

Consequently, while there are many methods known in the art for ultrasonically inspecting a welded portion of a joint during the welding process, none of those methods inspects the molten weld before solidification for determining corrective action to eliminate weld defects before the weld joint has solidified.

Therefore, what is needed is an ultrasonic weld inspection method that inspects the molten weld, inprocess, for determining if the molten weld contains a defect and then taking corrective action to eliminate the weld defect before the weld joint solidifies.

SUMMARY OF THE INVENTION

The ultrasonic weld inspection method comprises transmitting an ultrasonic pulse through the molten metal portion of the weld while the weld is being formed and determining if a weld defect is present in the molten metal. If no defect is detected in the molten metal, the welding process continues. However, if a defect is detected in the molten metal, the welding electrodes remain at that position and corrective measures are taken until the defect has dissipated. In this manner, defects are removed from the weld before the weld metal solidifies.

BRIEF DESCRIPTION OF THE DRAWINGS

While the specification concludes with claims particularly pointing out and distinctly claiming the subject matter of the invention, it is believed the invention will be better understood from the following description taken in conjunction with the accompanying drawings, wherein:

DESCRIPTION OF THE PREFERRED EMBODIMENT

In welding processes it is important to be able to detect weld defects in the molten weld metal so that the defects can be eliminated prior to the weld metal solidifying. The invention described herein provides a method for ultrasonically inspecting a weld joint during formation of the weld and provides a means to eliminate a defect detected in the molten weld metal before the weld metal solidifies.

Figure 1:
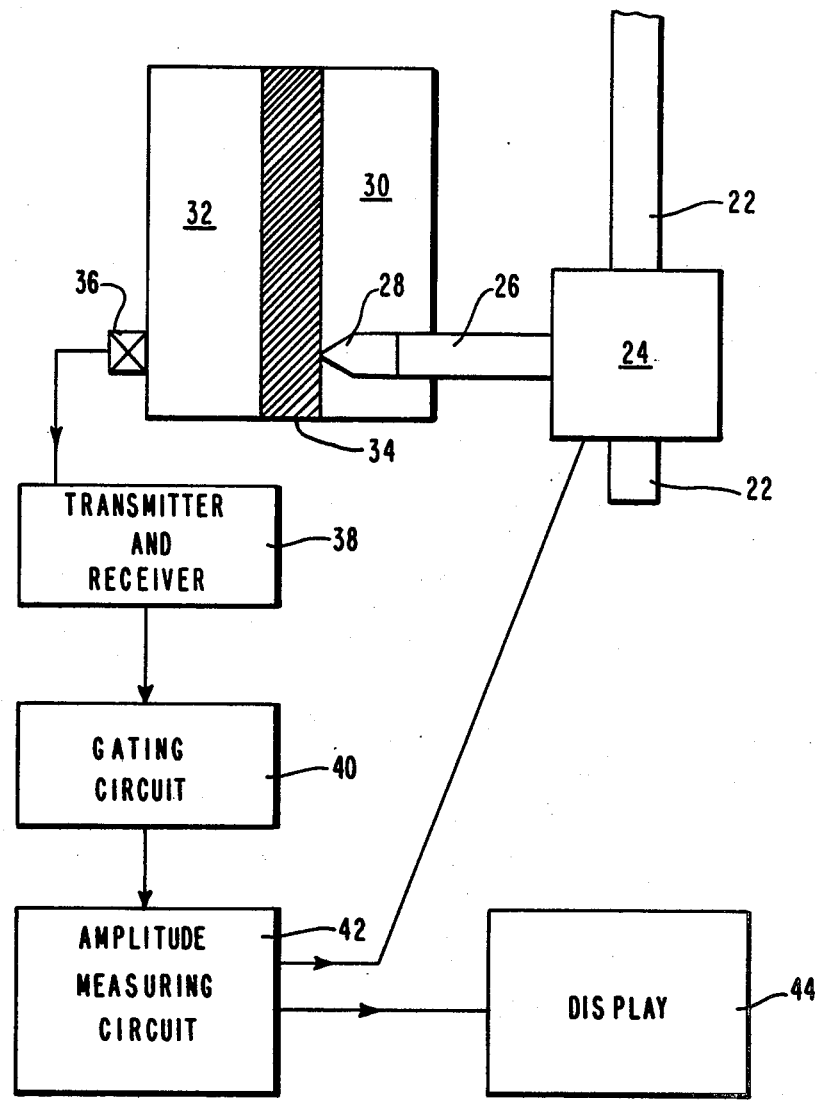
FIG. 1 is a schematic diagram of the weld inspection system.
Figure 2:
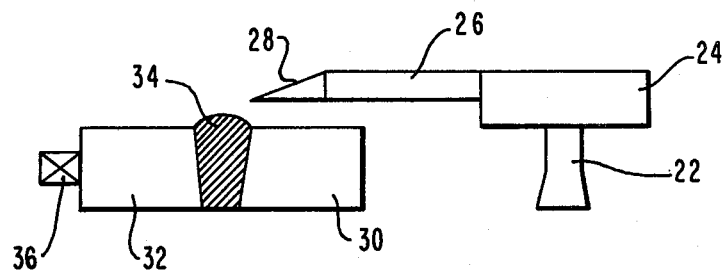
FIG. 2 is a side view of the weld inspection system.

Referring to FIGS. 1 and 2, the welding apparatus is referred to generally as 20 and comprises a guide rail 22 with a motorized carriage 24 mounted thereon. A weld arm 26 may be attached to carriage 24 and has a weld electrode 28 mounted on the end thereof. Carriage 24 which is capable of moving along guide rail 22 provides a means by which electrode 28 may be positioned for the welding process. In addition, a filler material may be used to form the weld joint.

A metal first member 30 and a metal second member 32 may be arranged to be welded by placing them in abutment with electrode 28 arranged near the interface of the members. When energized, electrode 28 establishes a puddle of molten metal 34 as is well known in the art. An ultrasonic transducer 36 which may be a 1 MHz longitudinal wave contact type transducer which may utilize an oil or water couplant may be moveably positioned near an end of second member 32 for producing and transmitting an ultrasonic pulse through second member 32 and through molten metal 34 and for being moved along second member 32 as electrode 28 is moved. The ultrasonic pulse is reflected at various points in second member 32 and molten metal 34 back to transducer 36. The reflected pulse can be used to identify defects in the molten metal 34.

The reflected signal received by transducer 36 is transitted to transmitter and receiver 38 which is then transmitted to gating circuit 40. Gating circuit 40, which may be chosen from those well known in the art, serves to transmit only reflected signals that correspond to selected locations in the members to be welded. For example, a gate may be provided that corresponds with the area of molten metal 34 so that defects in the molten metal 34 may be identified.

The selected signals from gating circuit 40 are transmitted to amplitude measuring circuit 42 which measures the amplitude of the reflected signals and compares them to a predetermined maximum allowable level. Of course, the maximum allowable level is predetermined in accordance with the particular types of materials used and the type of weld being formed. In any case, the maximum allowable level is chosen such that any reflected signal received by a selected gate and having an amplitude less than or equal to the maximum represents a void, inclusion, or other defect which is sufficiently small so as not to be detrimental to a satisfactory weld joint. If the amplitude of the reflected selected signal received by a selected gate exceeds the maximum allowable level, a defect in the molten metal 34 is indicated. In which case, a signal is transmitted to carriage 24 that maintains carriage 24 and electrode 28 at that location until the amplitude of the reflected signal is less than or equal to the maximum allowable level. If, however, the amplitude of the reflected signal is less than or equal to the maximum allowable level, the molten metal 34 is determined to be an adequate weld pool for formation of a reliable weld joint. Under these circumstances, a signal is transmitted to carriage 24 which causes carriage 24 to proceed along guide rail 22 thereby causing electrode 28 to proceed with the welding process.

During the welding process, the reflected signal's amplitude and the location of electrode 28 with respect to the members being welded may be displayed on display 44 which may be a video display or a paper chart display. In addition, the temperature of molten metal 34 may be monitored to prevent overheating of the weld zone.

Figure 3:
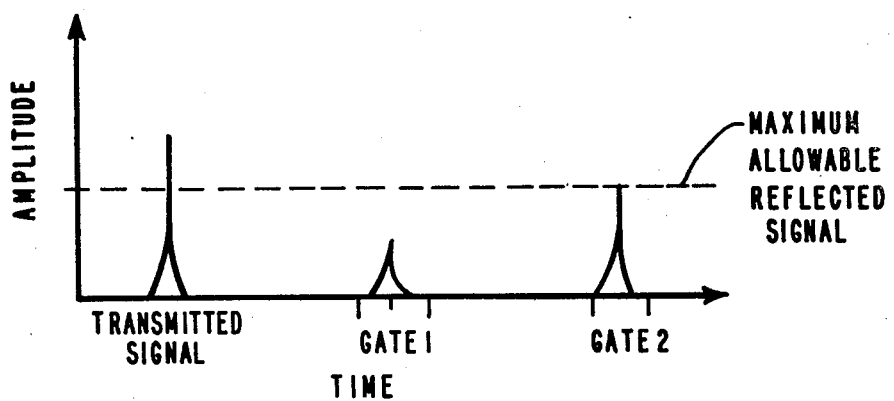
FIG. 3 is a graph of the amplitude of the reflected signals at selected locations illustrating an acceptable weld.
Figure 4:
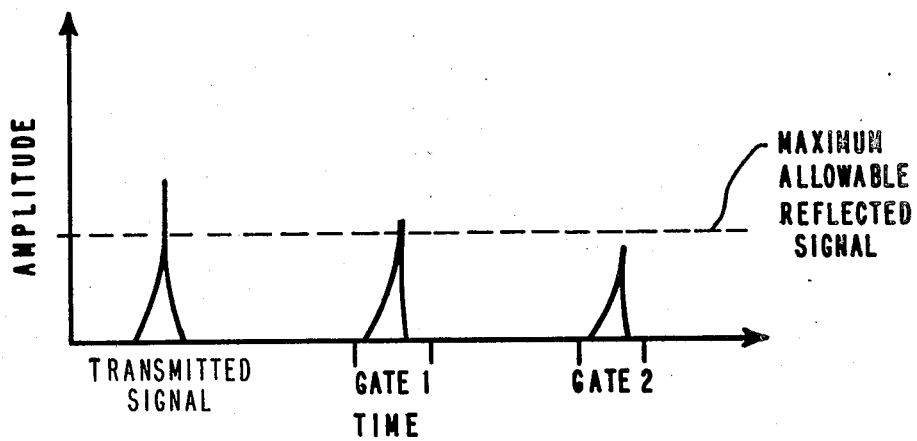
FIG. 4 is a graph of the amplitude of the reflected signals at selected locations illustrating an unacceptable weld.

Referring now to FIG. 3, a gate such as Gate 1 may be selected to correspond to the area of molten metal 34 and a gate such as Gate 2 may be selected to correspond to the end of first member 30. As shown in FIG. 3, the amplitude of the transmitted signal and the amplitude of the signal reflected from the end of first member 30 (Gate 2) may be displayed together with the amplitude of the signal reflected from molten metal 34 (Gate 1). When viewed as the welding process is in progress, an operator can readily determine when the molten metal 34 is in an acceptable condition as indicated by FIG. 3. In contrast, when a defect of an unacceptable size is present in molten metal 34, the signal reflected therefrom and indicated by Gate 1 in FIG. 4 exceeds the maximum allowable level thereby evidencing an unacceptable weld condition. Under these conditions, carriage 24 and electrode 28 are stopped and remain at that location until the defect in molten metal 34 is dissipated. By remaining in the location of the defect, the heat from electrode 28 tends to dissipate the weld defect while the weld metal remains molten. In this manner, a defect is not allowed to form in a solidified weld thereby eliminating the need to reweld or otherwise repair defective welds.

Figure 5:
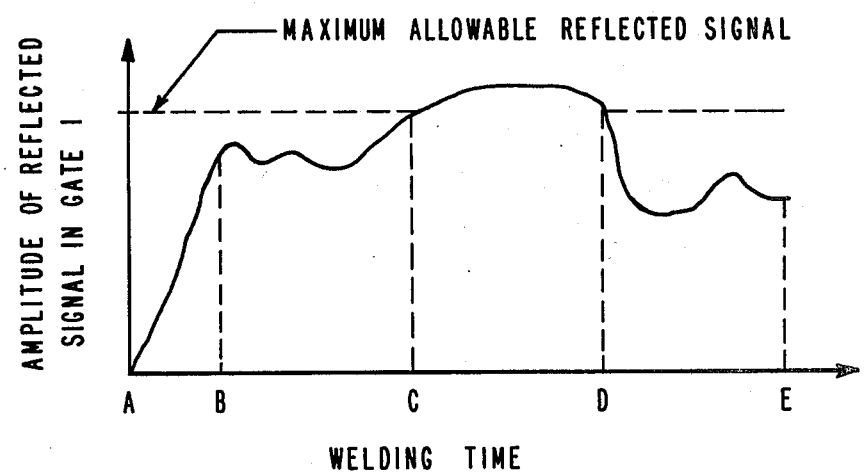
FIG. 5 is a graph of the amplitude of the reflected signal at Gate 1 during the welding process.

Referring to FIG. 5, a continuous display of the amplitude of the signal reflected in Gate 1 (molten metal 34) during the welding process is illustrated. Point A represents the beginning of the welding and inspection process in which the amplitude of the reflected signal in Gate 1 is zero. A typical Point B represents the amplitude of the reflected signal in Gate 1 during the welding process which is of an acceptable level. The time period from Point C to Point D represents an interval in which the amplitude of the reflected signal in Gate 1 exceeds the maximum allowable which indicates a defect. During this time period, electrode 28 remains at that point until the amplitude falls below the maximum (Point D). Point E represents the end of the welding process.

Therefore, it can be seen that the invention provides a means to inspect a weld as it is being formed so as to eliminate defects in the weld before the molten metal solidifies thereby eliminating the need to repair or reweld defective areas.

We claim as our invention:

1. A method for ultrasonically inspecting welds during the welding process comprising:
    moving a welding electrode relative to members to be welded thereby establishing a molten metal weld pool between said members;
    positioning an ultrasonic transducer near said molten metal weld pool for transmitting an ultrasonic signal to said molten metal weld pool and for receiving a reflected signal from said molten metal weld pool;
    selectively filtering said reflected signals from areas other than said molten metal weld pool and selectively accepting for comparison said reflected signals from said molten metal weld pool;
    comparing the amplitude of said accepted reflected signal to a predetermined maximum allowable amplitude for determining whether said accepted reflected signal is less than or equal to said maximum thereby indicating the absence of substantial defects in said molten metal weld pool; and
    maintaining said welding electrode at a given location until said accepted reflected signal is less than or equal to said maximum while maintaining said molten metal weld pool in liquid state thereby dissipating defects in said molten metal weld pool.

2. The method according to claim 1 wherein said method further comprises displaying the amplitudes of said accepted reflected signals.

* * * * *